US 6,582,418 B1

(12) United States Patent
Verbeek et al.

(10) Patent No.: US 6,582,418 B1
(45) Date of Patent: Jun. 24, 2003

(54) DRUG PUMP WITH REINFORCING GROOVES

(75) Inventors: Maurice T. Y. Verbeek, Geleen (NL); Frans Philippens, Beek (NL)

(73) Assignee: Medtronic, Inc., Minneapolis, MN (US)

( * ) Notice: Subject to any disclaimer, the term of this patent is extended or adjusted under 35 U.S.C. 154(b) by 217 days.

(21) Appl. No.: 09/585,493

(22) Filed: Jun. 1, 2000

(51) Int. Cl.[7] .................................................. A61K 9/22
(52) U.S. Cl. ............................ 604/892.1; 604/288.01; 604/288.04; 604/175; 604/93.01
(58) Field of Search .................... 604/892.1, 288.01, 604/288.02, 288.03, 288.04, 175, 93.01, 116, 151, 246

(56) References Cited

U.S. PATENT DOCUMENTS

| 3,527,220 A | | 9/1970 | Summers | |
|---|---|---|---|---|
| 3,951,147 A | | 4/1976 | Tucker et al. | |
| 3,987,790 A | * | 10/1976 | Eckenhoff et al. | 604/892.1 |
| 4,146,029 A | | 3/1979 | Ellinwood, Jr. | |
| 4,626,244 A | * | 12/1986 | Reinicke | 604/151 |
| 4,714,462 A | | 12/1987 | DiDomenico | |
| 4,838,887 A | | 6/1989 | Idriss | |
| 4,865,845 A | * | 9/1989 | Eckenhoff et al. | 604/892.1 |
| 4,931,050 A | | 6/1990 | Idriss | |
| 4,976,966 A | * | 12/1990 | Theeuwes et al. | 604/892.1 |
| 4,978,338 A | | 12/1990 | Melsky et al. | |
| 5,176,641 A | | 1/1993 | Idriss | |
| 5,207,666 A | | 5/1993 | Idriss et al. | |
| 5,209,746 A | * | 5/1993 | Balaban et al. | 604/892.1 |
| 5,234,424 A | * | 8/1993 | Yum et al. | 604/892.1 |
| 5,360,407 A | * | 11/1994 | Leonard | 604/175 |
| 5,370,635 A | * | 12/1994 | Strausak et al. | 604/892.1 |
| 5,433,710 A | * | 7/1995 | VanAntwerp et al. | 604/892.1 |
| 5,527,307 A | * | 6/1996 | Srisathapat et al. | 604/892.1 |
| 5,558,641 A | * | 9/1996 | Glantz et al. | 604/288.02 |
| 5,575,770 A | | 11/1996 | Melsky et al. | |
| 5,769,823 A | | 6/1998 | Otto | |
| 5,908,414 A | | 6/1999 | Otto et al. | |

FOREIGN PATENT DOCUMENTS

| EP | 0 600 948 B | 10/1996 |
|---|---|---|
| WO | WO 93/04714 A | 3/1993 |

* cited by examiner

*Primary Examiner*—Teresa Walberg
*Assistant Examiner*—Fadi H. Dahbour
(74) *Attorney, Agent, or Firm*—Stephen W. Bauer

(57) ABSTRACT

A pump for pumping drugs, medicaments or other liquids is disclosed having suture loops co-extensive with the outside wall of the pump. At least one depression is formed in the outside wall of the pump to strengthen the wall.

12 Claims, 8 Drawing Sheets

DRUG PUMP WITH REINFORCING GROOVES

BACKGROUND OF THE INVENTION

1. Field of the Invention

This invention relates to apparatus for delivering fluid drugs, medicaments or other medicinal liquids to a desired location within a human body and more particularly relates to means for reinforcing the surface structure of such devices.

2. Description of Related Art

A number of approaches have been followed in the prior art for the dispensing of medical substances in the body. One particularly effective method has been to implant a reservoir of fluid medical substances and a pump in a patient's body. The reservoir and pump are connected to a catheter that delivers the fluid medical substance to a desired location in the body.

A number of reservoirs, pumps and combinations of reservoirs and pumps have been developed. For example, U.S. Pat. No. 3,527,220 shows an implantable drug administrator that operates with a refillable bladder reservoir and a roller pump that is driven by a magnet located outside the body. U.S. Pat. No. 3,951,147 shows a reservoir formed from a bellows enclosed within a housing. The contents of the reservoir are pressurized by a fluorocarbon fluid located in the space between the housing and bellows. The unit continuously dispenses the liquid to the body site through a capillary tube.

U.S. Pat. No. 4,146,029 shows a dispenser that dispenses drugs in a predetermined manner which may be modified somewhat by means external to the body. A piston and bellows pumping device is used to dispense the drug.

Additional pumps and reservoirs are shown in U.S. Pat. No. 4,931,050, issued Jun. 5, 1990 to Samir F. Idriss entitled "Constant Pressure Variable Flow Pump"; U.S. Pat. No. 4,838,887, issued Jun. 5, 1990 to Samir F. Idriss entitled "Programmable Valve Pump"; U.S. Pat. No. 4,714,462, issued Jun. 5, 1990 to Robert A. DiDomenico entitled "Positive Pressure Programmable Infusion Pump"; U.S. Pat. No. 4,714,462, issued Jun. 5, 1990 to Samir F. Idriss entitled "Passive Shuttle Metering Device For Implantable Drug Delivery System"; and U.S. Pat. No. 5,176,641 issued Jan. 5, 1993 to Samir F. Idriss entitled "Implantable Drug Infusion Reservoir Having Fluid Impelling Resilient Foam Member".

Further pumps and reservoirs are shown in U.S. Pat. No. 5,575,770 issued Nov. 19, 1996 to Gerald S. Melsky and Bradley J. Enegren entitled "Implantable Drug Infusion System With Safe Bolus Capability"; U.S. Pat. No. 4,978,338 issued Dec. 18, 1990 to Gerald S. Melsky and Frank R. Prosl entitled "Implantable Infusion Apparatus"; U.S. Pat. No. 5,908,414 issued Jun. 1, 1999 to Karl-Heinz Otto, Manfred Wieland, Hans Baumann and Jorg-Roger Peters entitled "Implantable Infusion Pump"; and U.S. Pat. No. 5,769,823 issued Jun. 23, 1998 to Karl-Heinz Otto entitled "Implantable Infusion Pump". The collective teachings of the patents listed above are incorporated herein in their entireties by reference.

A number of approaches have been followed in the prior art for the dispensing of medical substances in the body. One particularly effective method has been to implant an implantable infusion pump 10 (FIG. 1) in a patient's body. The pump 10 has a reservoir 12 for storing the medical substances in the pump 10. Pump 10 is connected to a catheter 14 that delivers the fluid medical substance from the reservoir 12 to a desired location in the body. Such a pump 10 and catheter 14 combination is able to deliver the medical substance to a specific site in the body in tightly controlled, yet minute dosages. Both the pump 10 and catheter 14 are implanted within the body.

A typical pump 10 for storing and delivering fluid medicaments to a desired location in a body according to the present invention is shown in cross-section in FIGS. 2 and 3. As mentioned above, pump 10 stores and dispenses medical substances from a reservoir 12. Reservoir 12 is formed by a reservoir structure 16 having a reservoir structure upper end 18 and a reservoir structure terminal end 20. Reservoir structure 16 is typically a bellows 22 having pleated sides 24 and a substantially planar bottom 26 sealingly connected to the sides 24. Pleated sides 24 are made up of a series of inwardly directed annular rings 28 and outwardly directed annular rings 30 sealingly connected at inner connection points 32 and outer connection points 34. In the typical pump 10, bellows 22 terminates at its upper end 18 with an ultimate inwardly direct annular ring 36. Ultimate inwardly direct annular ring 36 terminates in a bellows terminal end 38 so that the bellows terminal end 38 is the reservoir structure terminal end 20 for a bellows type reservoir structure 16. Bottom 26 is usually circular so that bellows 22 is cylindrical. Because bellows 22 is cylindrical, bellows terminal end 38 is annular.

Bellows terminal end 38 is connected to an annular bracket 40. Viewed in cross-section, bracket 40 has a horizontal leg 42. Horizontal leg 42 has an inner terminal end 43 and an outer terminal end 44. Bellows terminal end 38 is connected to bracket 40 at 45 near the inner terminal end 43 by means well understood in the art such as welding. Annular bracket 40 also includes a vertical leg 46. Vertical leg 46 has an upper terminal end 47 and a lower terminal end 48. Horizontal leg 42 and vertical leg 46 are joined at outer terminal end 44 and upper terminal end 47, preferably by bending annular bracket 40 at outer terminal end 44 and upper terminal end 47 or by forming annular bracket to bend at outer terminal end 44 and upper terminal end 47. Bracket 40 greatly eases the manufacturing process of pump 10 as will be described hereafter.

Pump 10 also includes a bulkhead 50 having a top surface 52, a bottom surface 54 and an outer periphery 56. Pump 10 includes a metering system 58 usually attached to the top surface 52 of bulkhead 50. Metering system 58 may take the form of a peristaltic pump, a piston pump, a tubular or micro-machined capillary flow restrictor, a piezoelectric micropump or other metering means as will clear to those skilled in the art. Metering system 58 is connected to reservoir 12 through an output conduit 60.

The bottom surface 54 of bulkhead 50 includes an annular recess 62 extending into bulkhead 50 toward top surface 52. Recess 62 has an inner vertical wall 64 and a horizontal wall 65 connected together at 66. Recess 62 also has an outer vertical wall 67 connected to the horizontal wall 65 at 68. Horizontal leg 42 is about the same length as horizontal wall 66 while vertical leg 46 is about the same length as outer vertical wall 67. Bellows 22 is attached to bulkhead 50 at recess 62 by bracket 40 as described below.

Pump 10 also typically has a primary seal-sealing septum 70 through which a drug, fluid or other medicament is placed in the reservoir 12. A hypodermic needle can be inserted through the skin and through the primary seal-sealing septum 70 into a chamber 72 that is connected to reservoir 12 through an inlet conduit 74. Through the hypodermic needle, a quantity of a liquid agent, such as a medication, a growth factor, an antisense agent, an ionic solution, one or more antibodies, a hormone, proteins or peptides, viruses, cell suspension, a chemotherapeutic agent or toxin or some drug is inserted into the reservoir 12. The liquid agent is then delivered from reservoir 12 through the metering system 58 and through catheter 14 that is attached to pump 10 through a catheter conector 76 that is attached to the metering system 58. The catheter 14 is positioned to deliver the agent to infusion sites in the patient's body.

Pump 10 may also have a catheter access port septum 78 through which a bolus injection of drug, fluid or other medicament may be administered directly to the patient through the catheter 14, bypassing the metering system 58. Catheter access port septum 78 may also be used to take a sample of cerebrospinal fluid (CSF) from catheter 14 or for checking the patency of catheter 14 in the event of a loss of therapeutic benefit.

Pump 10 also includes an upper case 80 and a lower case 82 that substantially defines the outer dimensions of pump 10 and protects the inner parts, bellows 22, bulkhead 50 and metering system 58, of pump 10. Upper and lower cases 80, 82 are typically attached to the bulkhead 50 at the outer periphery 56 of the bulkhead 50 by means such as welding. Lower case 82 has a bottom surface 86 and a side wall 88.

A propellant chamber 90 is placed between lower case 82 and the reservoir structure 16. A propellant gas is place in propellant chamber 90. The propellant gas acts as a pressure-providing means to the reservoir structure 16 that compresses the reservoir structure 16 to discharge the drug or other agent stored in the reservoir 12. The propellant gas used to drive such a "gas driven" pump 10 is a fluid that is in phase change between a liquid state and a gas state when, i.e., in equilibrium between phases at around 35–37 degrees (Celsius), which is the usual temperature range of the human body.

In a particular type of pump 10, metering system 58 takes the form of a tubular or micro-machined capillary flow restrictor. In such a pump, the medical substance is dispensed from the reservoir 12 at a constant rate that depends primarily on the geometry of the tubular or micro-machined flow restrictor. In such a pump 10, it is relatively important that the pressure in propellant chamber 90 be maintained at a higher pressure than is necessary in a pump 10 having a metering system 58 comprising a peristaltic pump, a piston pump or a piezoelectric micropump. For example, the propellant pressure in a peristaltic pump such as the Synchromed® pump manufactured and sold by Medtronic, Inc. of Minneapolis, Minn. is about 0.276 bar (4.00 Psi). On the other hand, the propellant pressure in a constant rate pump having a tubular flow restrictor such as the Isomed® pump also manufactured and sold by Medtronic, Inc. of Minneapolis, Minn. is about 2.10 bar (30.46 Psi). The reason for a higher pressure in the propellant chamber 90 in a constant rate pump 10 with a capillary tube flow restrictor is that this higher pressure reduces the variability in flow rates of the drug or other agent due to atmospheric conditions such as barometric pressure.

In manufacturing pump 10, the bellows terminal end 38 of bellows 22 is attached to the horizontal leg 42 of bracket 40 near the inner terminal end 43 by means such as welding. Since both bellows terminal end 38 and bracket 40 are annular, bellows terminal end 38 is connected to bracket 40 around an annular path as connection point 45 is moved around horizontal leg 42. At this stage of the manufacturing process, access to connection point 45 is relatively free since bellows 22 has not yet been joined to bulkhead 50.

Once bellows terminal end 38 has been joined to horizontal leg 42 of bracket 40, bracket 40 is moved onto horizontal wall 66 of recess 62. As described above, horizontal leg 42 is about the same length as horizontal wall 66. This allows bracket 40 to be moved into recess 62 so that the inner terminal end 43 of horizontal leg 42 comes into contact with horizontal wall 66. In this position, vertical leg 46 also comes into contact with outer vertical wall 67. Bracket 40 is then connected to the recess 62 at lower terminal end 48 by means such as welding around the entire annular lower terminal end 48. In this way, bellows 22 is sealingly attached to bulkhead 50 at lower terminal end 48 of bracket 40.

After a pump 10 is manufactured and before the pump 10 can be used as a medical device, the pump 10 must be thoroughly sterilized. One part of the sterilization process involves heating the pump 10 to a relatively high temperature for a relatively long period of time with the propellant in the propellant chamber 90. For example, in the Isomed® pump mentioned above, the pump 10 is heated to about 124 Celsius (255.2° F.) for about 30 minutes. This heating results in an increase in the pressure in the propellant chamber from about to about 7 bar (101.5 Psi). This pressure is exerted, among other parts of the pump 10, on the lower case 82.

If the walls of the lower case 82 have the same thickness everywhere, as the pressure increases in the propellant chamber 90, the walls of the lower case 82 often deforms or bulges out under the pressure. This is clearly not a desirable condition.

To remedy this deformation problem, a reinforcing plate 92 has been added to the bottom surface 86 of lower case 82. Reinforcing plate 92 is typically a disk shaped or annular plate that is either attached to the bottom surface 86 or formed in the bottom surface 86. Reinforcing plate 92 substantially covers the entire bottom surface 86 and has a thickness such that reinforcing plate 92 prevents deformation of the lower case 82. Reinforcing plate 92 is typically welded to the bottom surface 86. Reinforcing plate 92 has the effect of creating a thicker portion of the bottom surface 86 where the reinforcing plate is present than would be present were not the reinforcing plate 92 used. Because the bottom surface 86 is thicker with reinforcing plate 92, bottom surface 86 is able to more easily withstand the high pressures caused by the heating process without the undesirable deformation.

Unfortunately, the function of strengthening the bottom surface 86 by the reinforcing plate 92 is needed only during the heating process. After the heating process is complete, the reinforcing plate 92 merely adds size and weight to the pump 10. Further, the addition of a reinforcing plate 92 adds a part and requires the additional manufacturing step of welding the reinforcing plate 92 to the bottom surface 86. It is desirable to make the pump 10 as small and light as possible and as cheap and easy to manufacture as possible. Therefore, it is highly desirable to make a pump 10 that may be autoclaved without buckling the lower case 82 and that does not require a reinforcing plate 92.

SUMMARY OF THE INVENTION

A pump for pumping drugs, medicaments or other liquids is disclosed having surface recesses placed in the outer surface of the lower case. The recesses reinforce the lower case sufficiently to remove a reinforcing plate.

It is therefore an object of the present invention to provide a pump that does not require a reinforcing plate to allow the lower case to withstand the pressure of heating the pump as part of the sterilization process.

These and other objects of the invention will be clear from the description of the invention contained herein and more particularly from the description in conjunction with the drawings attached hereto. Throughout this description, wherever referred to, like elements are referred to by like reference numbers.

BRIEF DESCRIPTION OF THE DRAWINGS

The advantages of the present invention will become more apparent by referring to the following detailed description and accompanying drawings, in which.

DESCRIPTION OF THE PREFERRED EMBODIMENT

Figure 1:
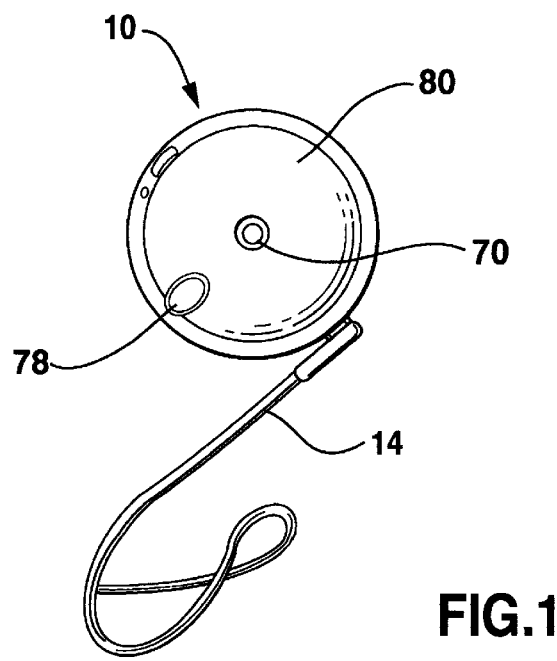
FIG. 1 is a schematic view of a typical pump and catheter.
Figure 4:
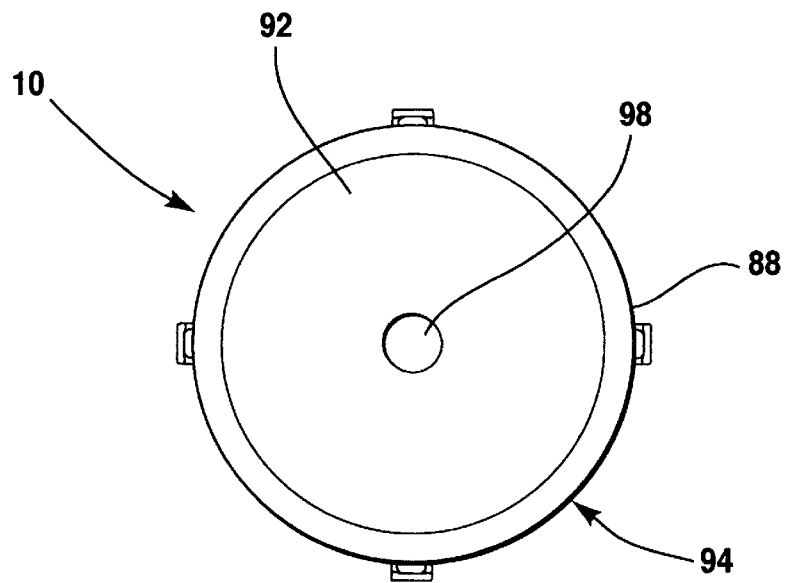
FIG. 4 is a top view of the lower case of the drug pump of FIG. 2.
Figure 2:
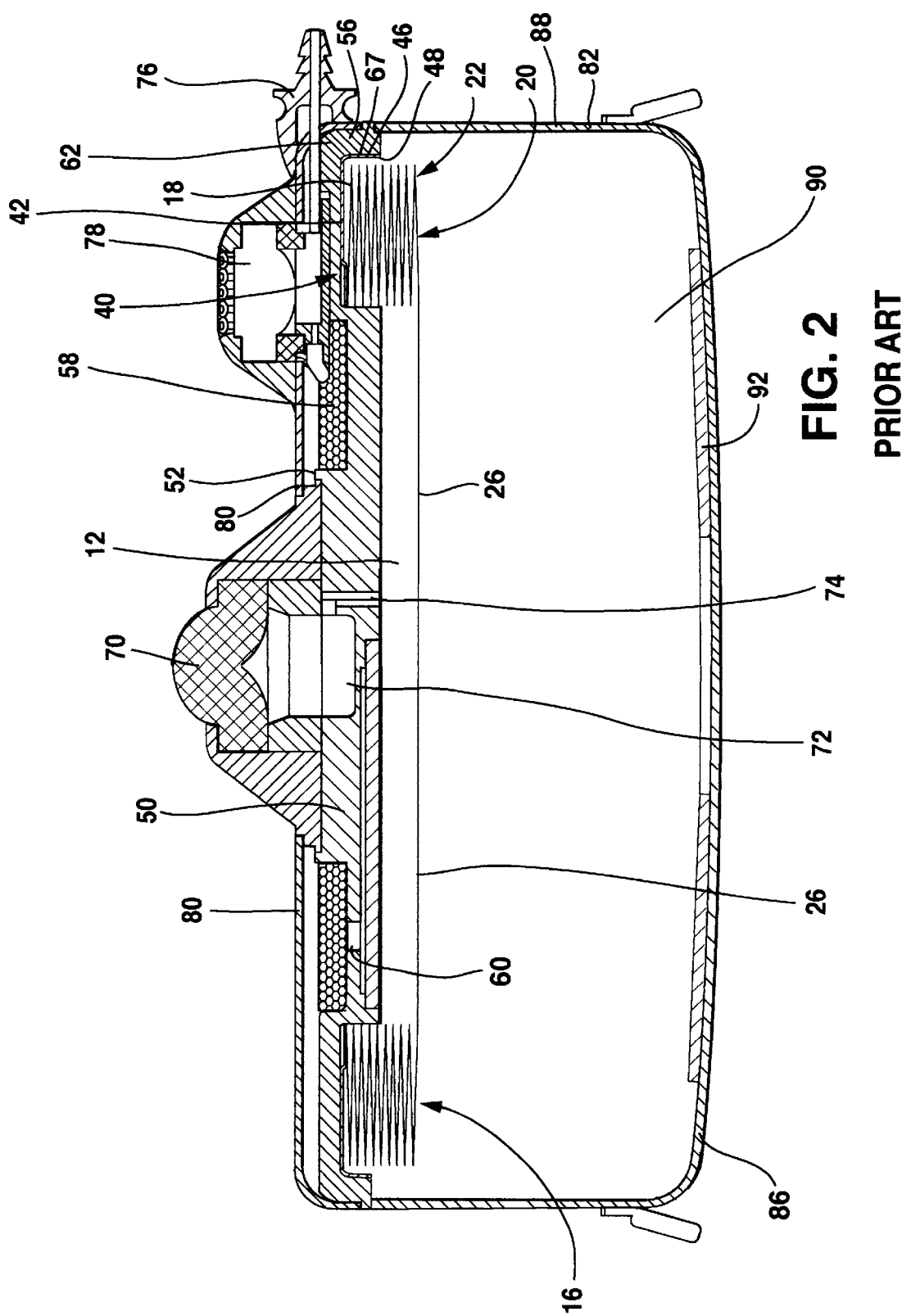
FIG. 2 is a side cross-sectional view of a typical prior art drug pump with a reinforcing plate.
Figure 3:
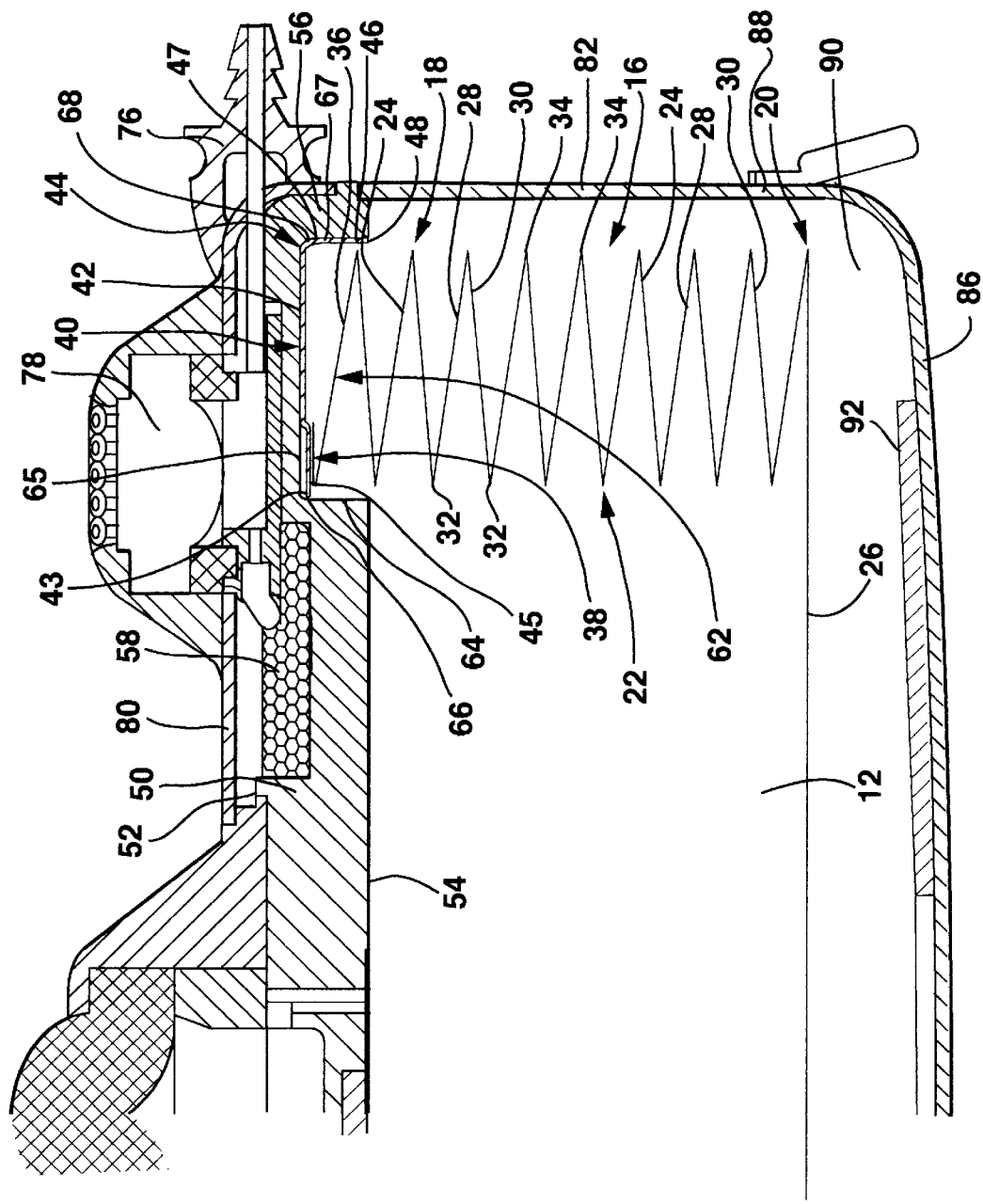
FIG. 3 is a close-up side cross-sectional view of the prior art drug pump of FIG. 2.
Figure 5:
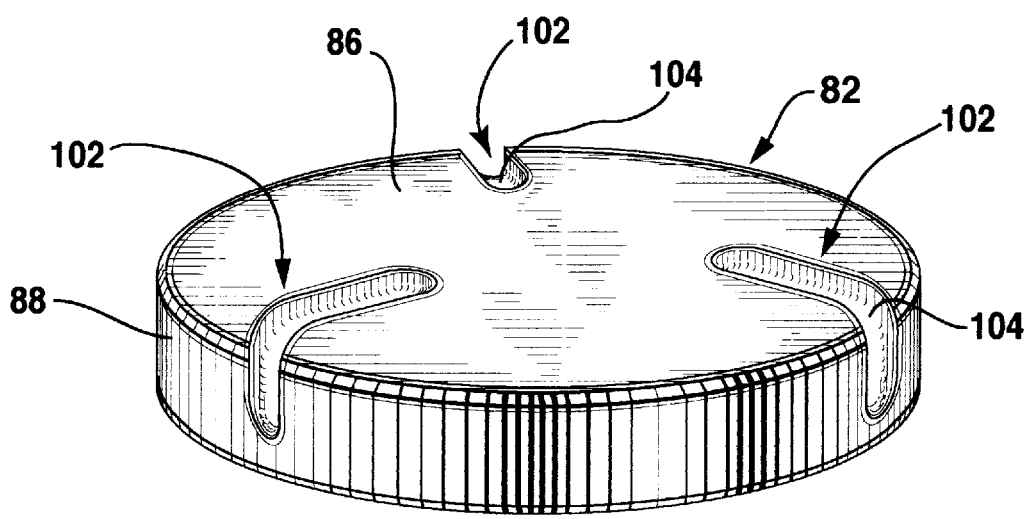
FIG. 5 is a perspective view of the bottom of the drug pump of the present invention.

Referring now to FIGS. 5–9, a drug pump 10 incorporating the present invention is shown. As can be seen, pump 10 has a lower case 82 having an outside wall 94, an interior 96 and central axis 98. In the embodiment shown in FIGS. 5–9, pump 10 is substantially disk shaped with bottom surface 86 of lower case 82 transitioning to side wall 88 at 100. Side wall 88 is roughly equidistant from the central axis 98.

Although pump 10 is shown as being disk shaped to illustrate the present invention, this is not a requirement for the present invention. In fact, any shape for pump 10 may make use of the present invention so long as pump 10 has an outside wall 94. In pumps that are not disk shaped, central axis 98 merely indicates an approximate center of pump 10.

Figure 6:
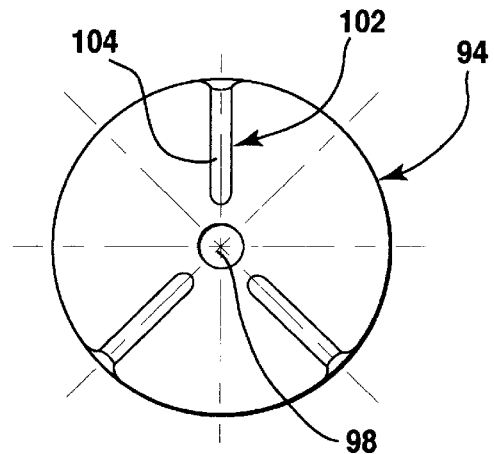
FIG. 6 is a bottom view of the lower case of the drug pump of FIG. 5.
Figure 7:
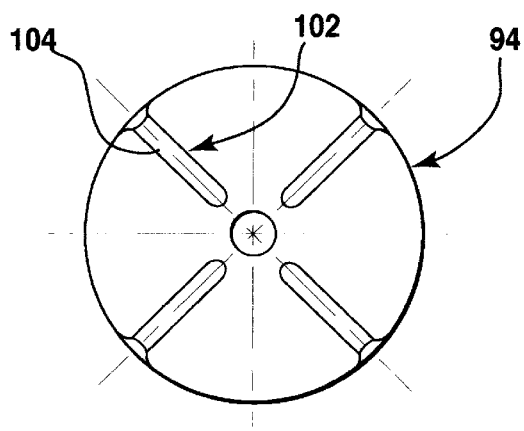
FIG. 7 is a bottom view of an alternate embodiment of the drug pump of FIG. 5.
Figure 8:
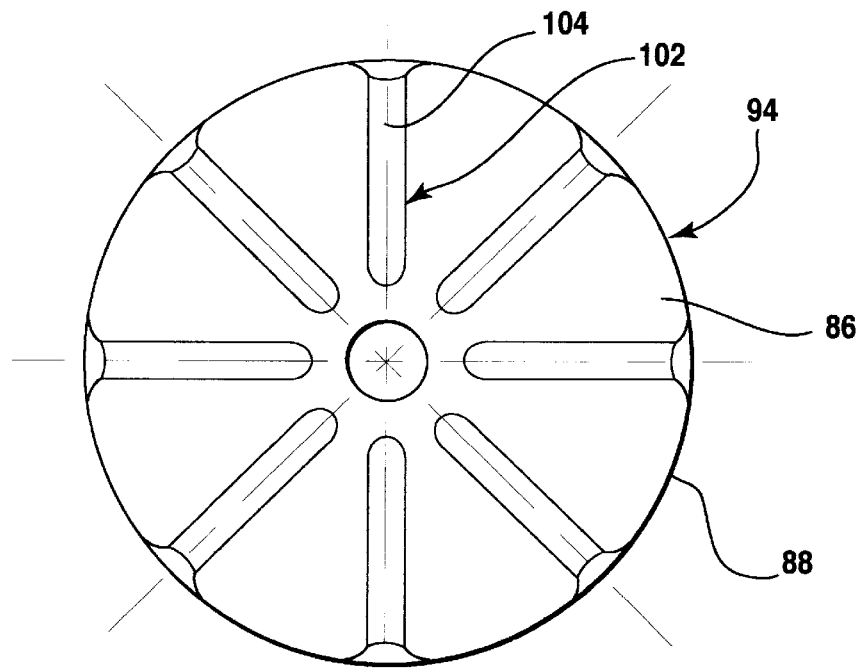
FIG. 8 is a bottom view of an alternate embodiment of the drug pump of FIG. 5.
Figure 9:
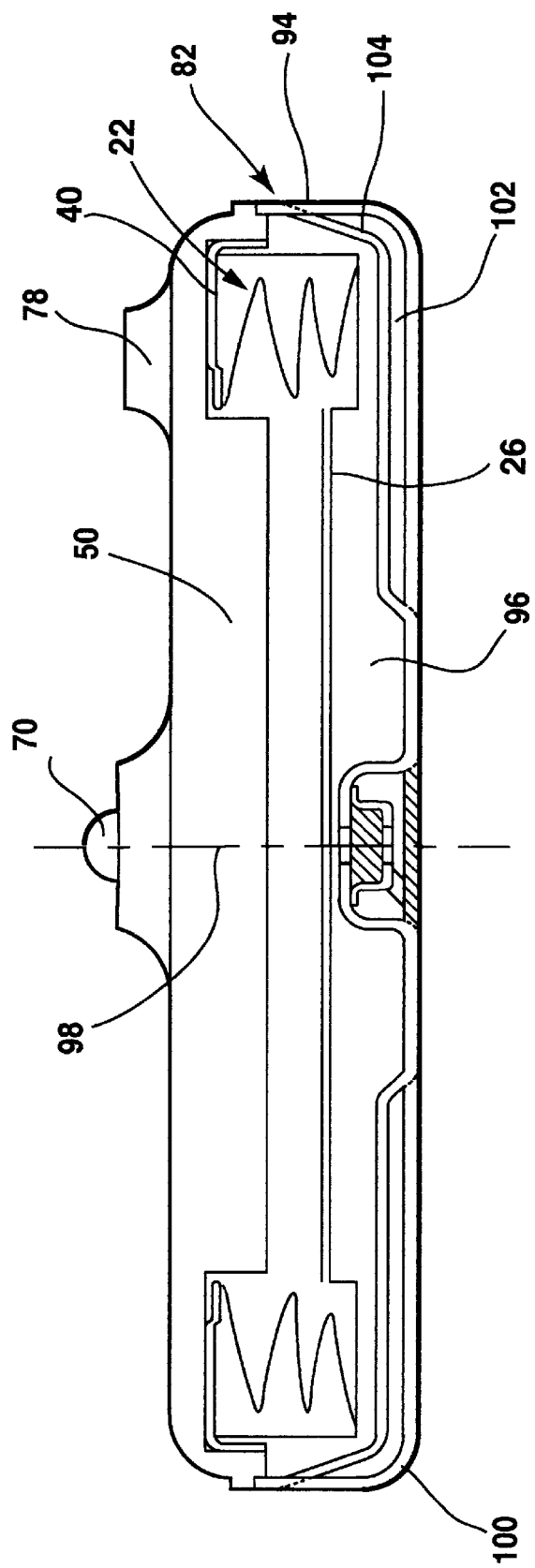
FIG. 9 is a side cross-sectional view of the lower case of the drug pump of FIG. 5.

In the present invention, the outside wall 94 of pump 10 contains at least one depression 102 that extends inwardly from the outside wall 94 toward the interior 96. In the preferred embodiment, several depressions 102 are located at sites on the outside wall 94. For example, FIG. 6 shows three depressions 102 equally spaced around the outside wall 94. More or fewer depressions 102 may be used as desired. For example, FIGS. 7–8 show four and eight depressions 102 to show but a few possible variants. Further, the depressions 102 may also be non-equally spaced.

Depressions 102 are preferably shallow depressions in the lower case 82 forming a depression surface 104. In the embodiment shown in FIGS. 5–9, depressions 102 are formed in the lower case 82 in both the bottom surface 86 and side wall 88 where the side wall 88 transitions to the bottom surface 86 of pump 10. Also in the embodiment shown in FIGS. 5–9, the depression surface 104 is convex with respect to the interior 96 of pump 10. Alternately, the depression surface 104 may be concave with respect to the interior 96 of pump 10 or any other shape so long as the depression surface 104 forms a depression 102.

Figure 10:
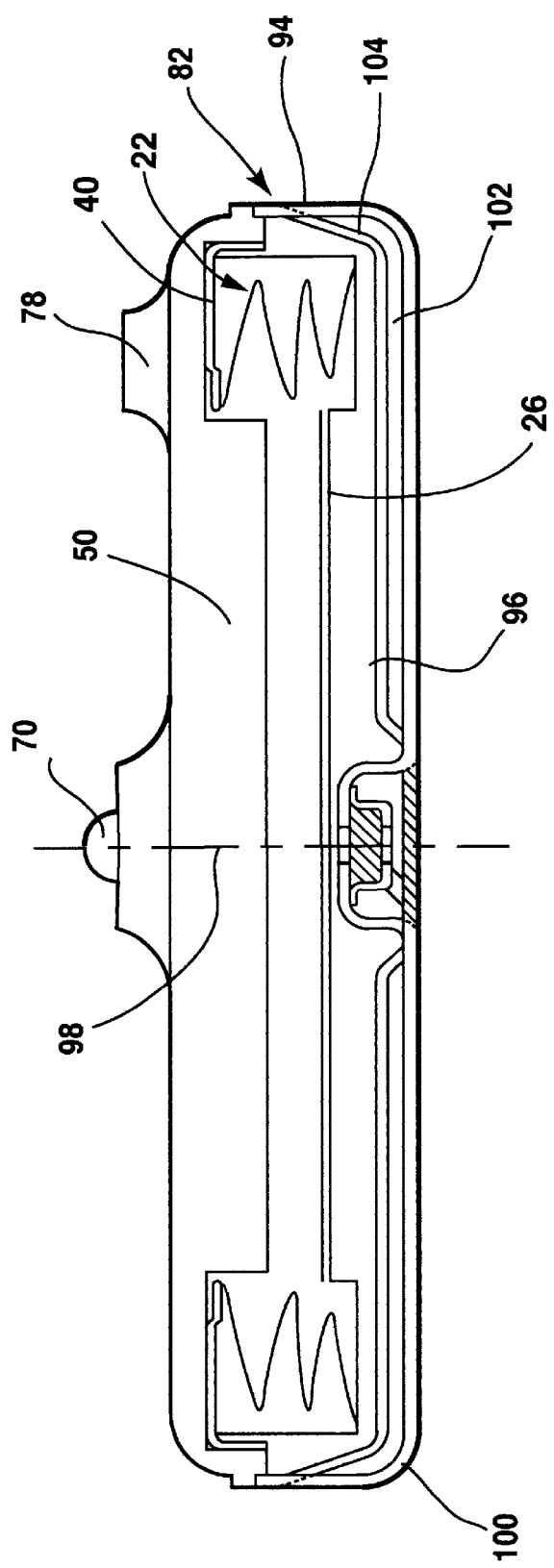
FIG. 10 is a side cross-sectional view of an alternate embodiment of the lower case of the drug pump of FIG. 5.
Figure 11:
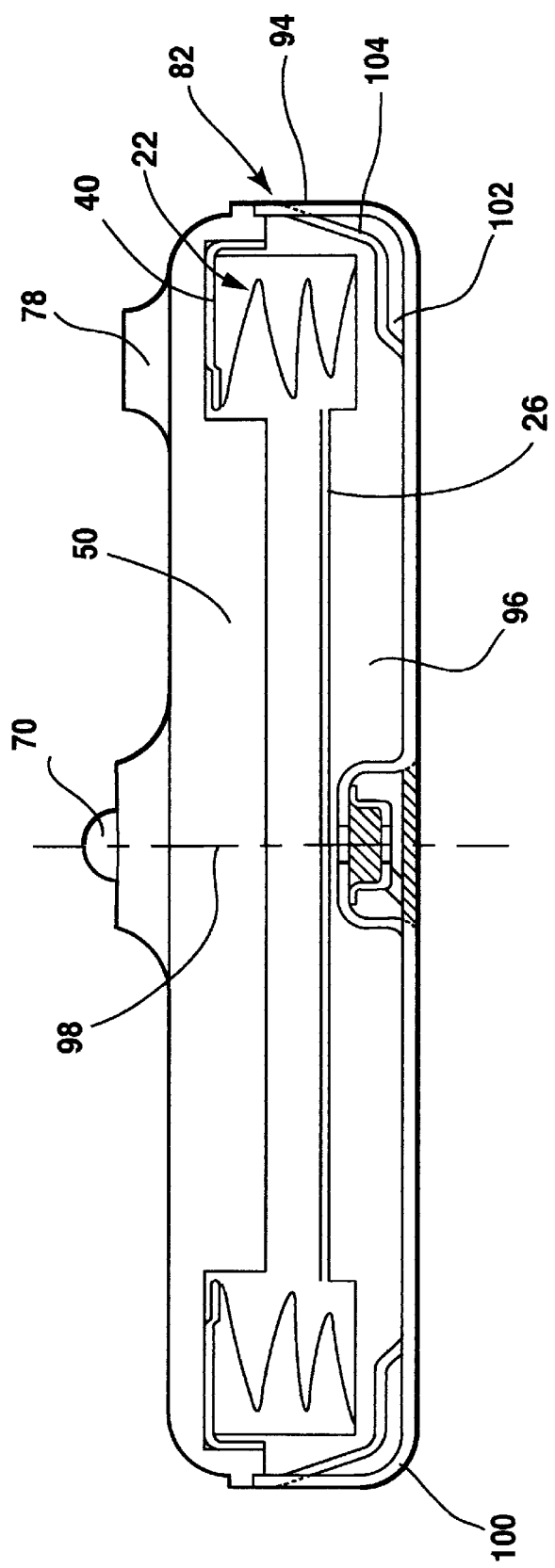
FIG. 11 is a side cross-sectional view of an alternate embodiment of the lower case of the drug pump of FIG. 5.

Depressions 102 may have any depth toward the interior 96 from the bottom surface 86 or side wall 88 although a preferable depth of depressions 102 is about 1.5–2.00 mm measured from the outside wall 94 toward the interior 96. It is recognized that depressions extend into the interior 96 into the propellant chamber 90. As a result, the only limitation on the depth of depressions 102 is the deformation capability of the material of the lower case 82 and the desire to preserve space in the propellant chamber 90 resulting from the intrusion of depressions 102 into propellant chamber 90.

Where depressions 102 are formed in the bottom surface 86 of lower case 82, depressions 102 preferably extend a significant distance toward the central axis 98 of the pump 10 as shown in FIGS. 5–9. However, depressions 102 may extend a greater (FIG. 10) or lesser (FIG. 11) distance on the bottom surface 86 from the side wall 88 toward or through the central axis 98 or may extend across the bottom surface oblique to the central axis. Further, although depressions 102 have been described as being formed in the bottom surface 86 and side wall 88, depressions 102 may be formed exclusively in the bottom surface 86, side wall 88 or in the upper case 80 or in any combination of these.

Although the preferred embodiment of depressions 102 is a groove, depressions 102 may take any form so long as the depression surface 104 is moved toward the interior 96 of pump 10 from the ordinary outside wall 94 of the pump 10. For example, depressions 102 make take the form in cross-section of semi-spherical depressions or truncated discoid depressions to name but a possible few configurations in addition to the trough-like depressions 102 described above. Whatever the form of depressions 102, the primary function of depressions 102 is to form a shallow depression from the outside wall 94. These depressions 102 substantially strengthen lower case 82 without the need for a reinforcing plate 92.

The description contained herein is intended to be illustrative of the invention and not an exhaustive description. Many variations and alternatives to the disclosed embodiments will occur to one of ordinary skill in this art. All these alternatives and variations are intended to be included within the scope of the attached claims. Those familiar with the art may recognize other equivalents to the specific embodiments described herein which equivalents are also intended to be encompassed by the claim attached hereto.

I claim:

1. In an implantable medical device for infusing drugs, medicaments or other liquids into a body, the medical device having a reservoir for the storage of a drug, medicament or other liquid, means operatively coupled to the reservoir for dispensing the drug, medicament or other liquid, an outer shell encasing the reservoir and the means for dispensing the drug, medicament or other liquid, the outer shell having an outside wall, the medical device having an interior, and a propellant chamber defined between the reservoir and the outer shell in which pressurized gas exerts positive pressure against the resevoir, the improvement comprising:

wherein, the outside wall has at least one depression extending toward the interior from the outside wall, the depression having a depression surface, to reinforce the outer shell particularly against increased pressure in the propellant chamber during heat sterilization.

2. The medical device of claim 1 wherein the number of depressions is at least two.

3. The medical device of claim 2 wherein the at least two depressions are equally spaced around the outside wall.

4. The medical device of claim 2 wherein the at least two depressions are non-equally spaced around the outside wall.

5. The medical device of claim 1 wherein the depression surface is convex with respect to the interior of the medical device.

6. The medical device of claim 1 wherein the depression surface is concave with respect to the interior of the medical device.

7. An implantable medical device for infusing drugs, medicaments or other liquids into a body, the medical device comprising:

a reservoir for the storage of a drug, medicament or other liquid;

means operatively coupled to the reservoir for dispensing the drug, medicament or other liquid;

an outer shell encasing the reservoir and the means for dispensing the drug, medicament or other liquid, the outer shell having an outside wall, the medical device having an interior; and a propellant chamber defined by the reservoir and the outer shell in which pressurized gas exerts positive pressure against the resevoir the outside wall of the outer shell having at least one depression extending toward the interior from the outside wall, the depression having a depression surface, to reinforce the outer shell particularly against increased pressure in the propellant chamber during heat sterilization.

8. The medical device of claim 7 wherein the number of depressions is at least two.

9. The medical device of claim 8 wherein the at least two depressions are equally spaced around the outside wall.

10. The medical device of claim 8 wherein the at least two depressions are non-equally spaced around the outside wall.

11. The medical device of claim 7 wherein the depression surface is convex with respect to the interior of the medical device.

12. The medical device of claim 7 wherein the depression surface is concave with respect to the interior of the medical device.

* * * * *